Figure 2:
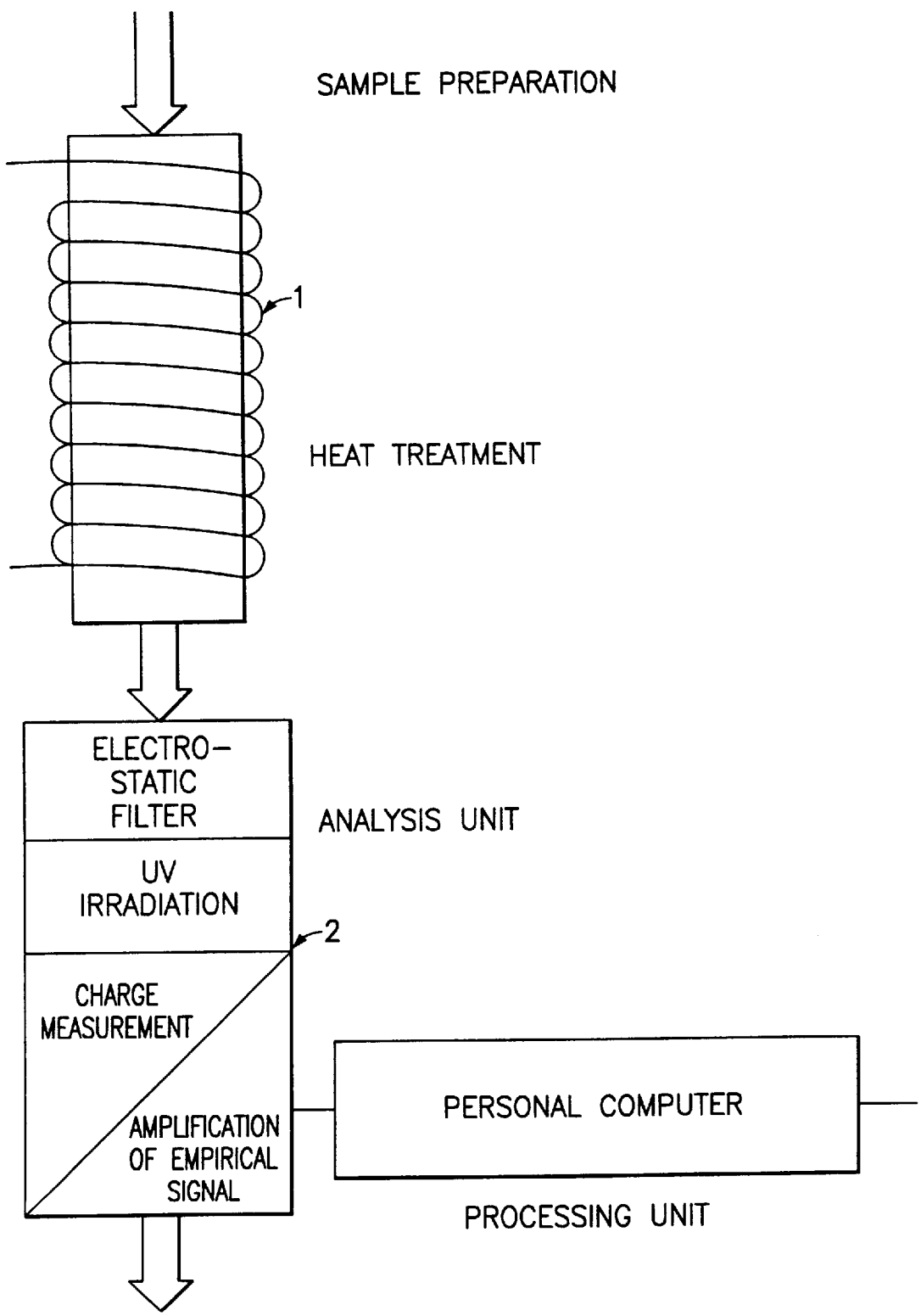
Figure 3A:
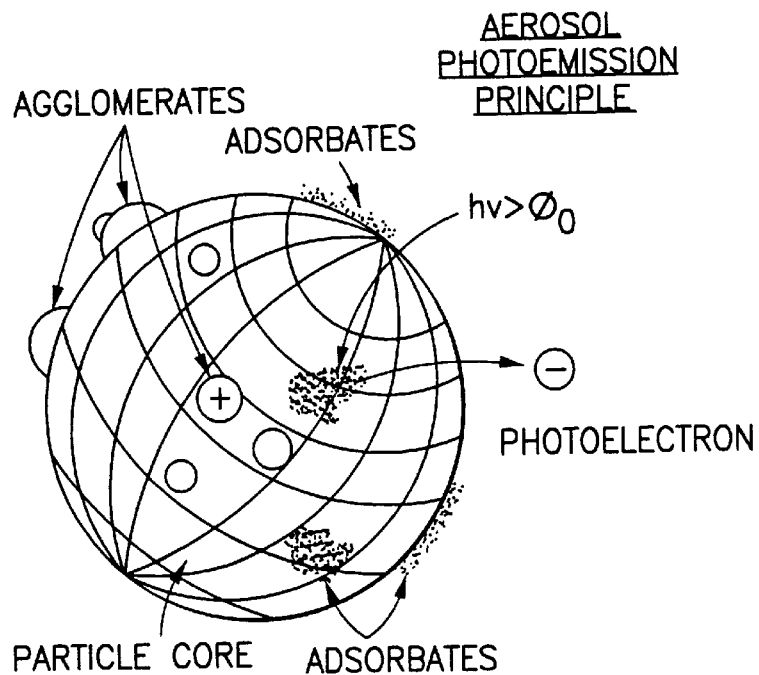
Figure 3B:
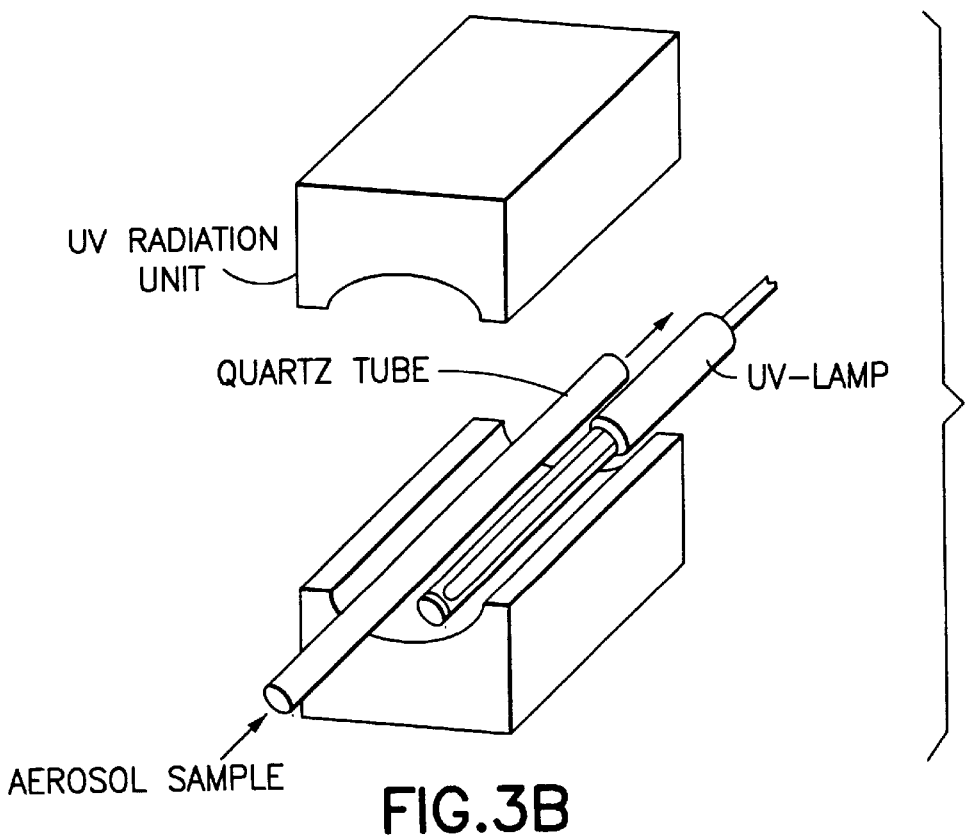
Figure 4:
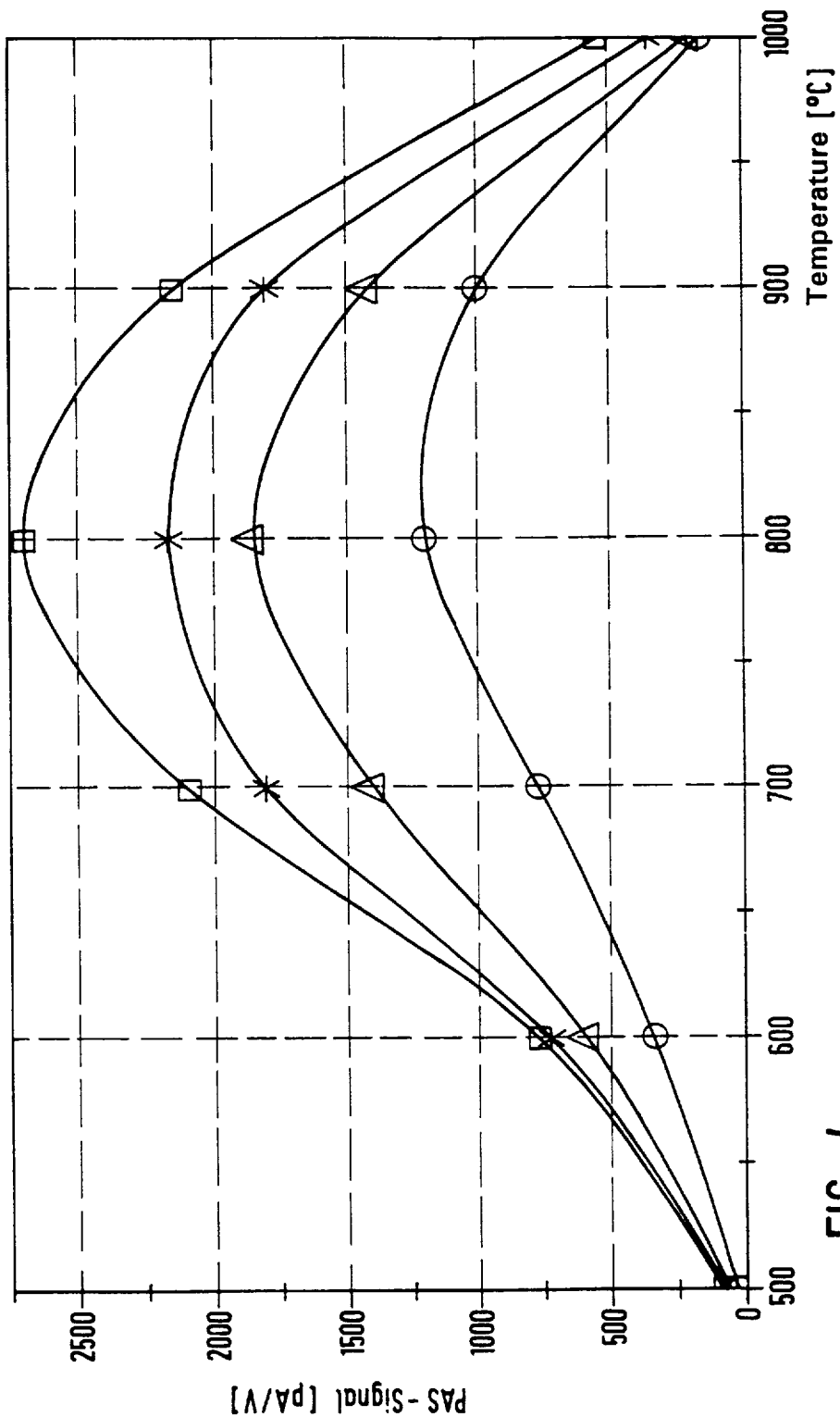
Figure 5:
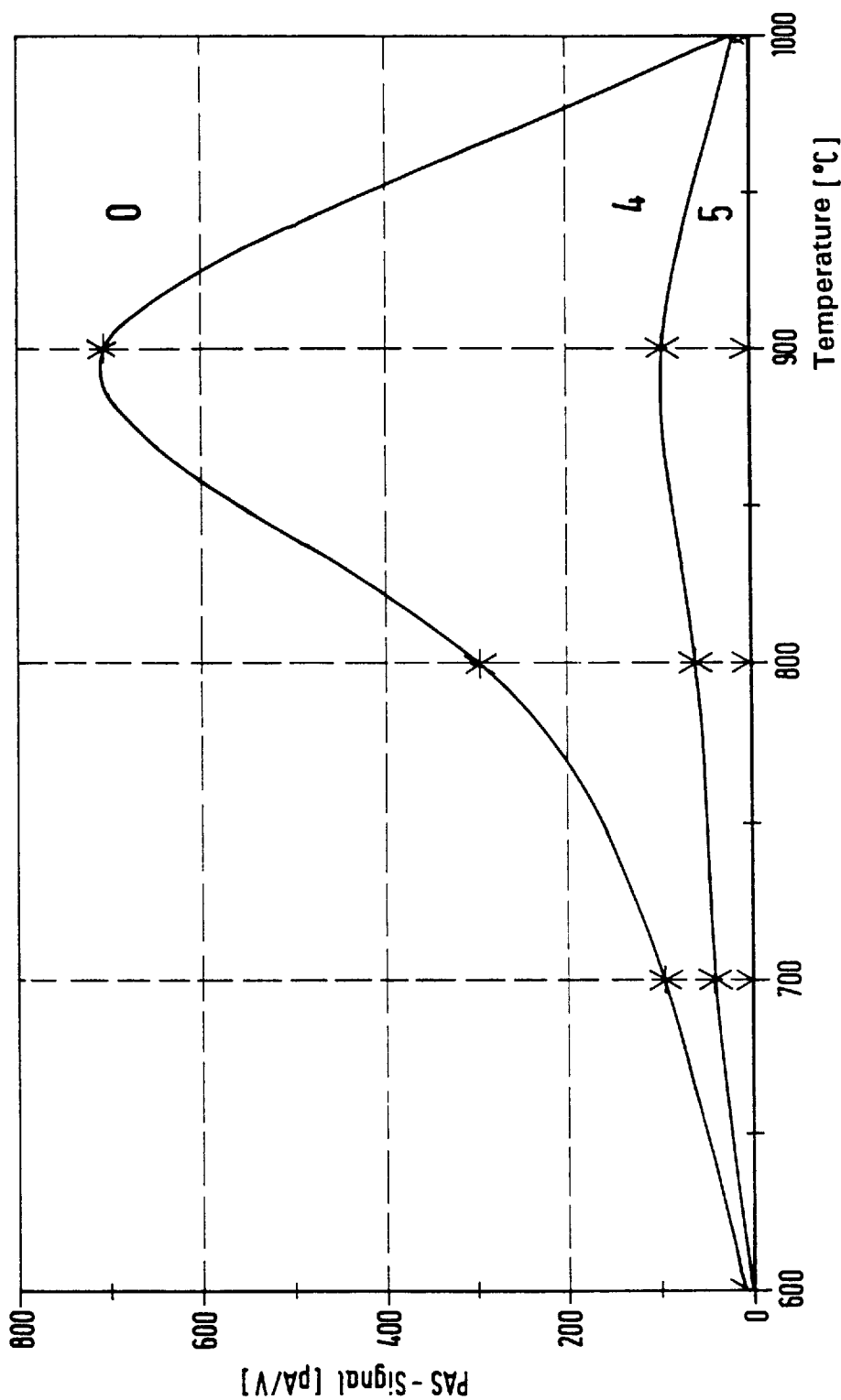

United States Patent

Hackfort et al.

[11] Patent Number: 5,861,629
[45] Date of Patent: Jan. 19, 1999

[54] METHOD OF AND DEVICE FOR THE QUANTITATIVE DETECTION OF MATERIAL IN A SAMPLE

[75] Inventors: Helmut Hackfort, Köln; Georg Hinzen, Aachen, both of Germany

[73] Assignee: Forschungszentrum Jülich GmbH, Germany

[21] Appl. No.: 571,908

[22] PCT Filed: Jun. 24, 1994

[86] PCT No.: PCT/DE94/00731

§ 371 Date: Jun. 18, 1996

§ 102(e) Date: Jun. 18, 1996

[87] PCT Pub. No.: WO95/01563

PCT Pub. Date: Jan. 12, 1995

[30] Foreign Application Priority Data

Jun. 29, 1993 [DE] Germany ............. 43 21 456.8

[51] Int. Cl.$^6$ ................................. G01N 23/227
[52] U.S. Cl. ................... 250/372; 250/379; 250/382; 250/423 P
[58] Field of Search ................. 250/379, 382, 250/383, 423 P, 372; 324/464

[56] References Cited

U.S. PATENT DOCUMENTS

| | | |
|---|---|---|
| 4,355,231 | 10/1982 | Laver et al. ............. 250/341.6 X |
| 4,590,376 | 5/1986 | Smith ........................ 250/372 |
| 4,769,548 | 9/1988 | Burtscher et al. ............. 250/423 P |
| 4,837,440 | 6/1989 | Burtscher et al. ............. 250/379 |
| 4,959,010 | 9/1990 | Burtscher et al. ............. 250/283 |

FOREIGN PATENT DOCUMENTS 34 22 054 12/1985 Germany .

OTHER PUBLICATIONS

Weeks et al, "Interaction of TEA $CO_2$ Laser Radiation with Aerosol Particles", Applied Optics, 15 (11), pp. 2917–2921, Nov. 1976.

Burtscher et al, "Probing Aerosols by Photoelectric Charging", J. Appl. Phys., 53(5), pp. 3787–3791, May 1982.

Primary Examiner—Edward J. Glick
Attorney, Agent, or Firm—Frishauf, Holtz, Goodman, Langer & Chick, P.C.

[57] ABSTRACT

Method of quantitatively detecting material in a sample, whereby the material is in the form of submicrometric particles covered by a photoemitting substance, and a device for practicing the method. The material in the sample is heated to a photoemitting state and subjected while in that state to photoemission measurement. The proportion of material in the sample is determined from the signal obtained from that measurement by comparison with empirical data obtained from a reference sample containing a previously detected quantity of the material or by comparison with data obtained for the material by calibration.

18 Claims, 6 Drawing Sheets

FIG.1

FIG.6

METHOD OF AND DEVICE FOR THE QUANTITATIVE DETECTION OF MATERIAL IN A SAMPLE

The present invention concerns a method of and a device for the quantitative detection of material in a sample. The material is in the form of submicrometric particles covered by a photoemitting substance.

Such a method and device would be useful in many applications, for detecting how much coal there is in a fuel that is to be burned for example or how much organic material there is in a foodstuff or other sample.

Obtaining surface-specific information about floating particles by measuring photoemission is known from German 3 422 054 C2. The procedure comprises the quantitative detection of substances that evaporate off the particles at a specific temperature. The signal detected in the photoemission section of the apparatus is employed as a measure of how much material has precipitated onto the surface of the aerosol.

One object of the present invention on the other hand is to provide a method that will allow detection of the proportion of the material the sample consists of. Another object of the present invention is a device for carrying out the method.

The first object is attained in accordance with the present invention in that the material in the sample is heated to a photoemitting state and subjected while in that state to photoemission measurement, and the proportion of material in the sample is determined from the signal obtained from that measurement in conjunction with empirical data obtained from a reference sample containing a previously detected quantity of the material or by using data obtained for the material by calibration.

Research (cf. the discussion of the figures hereinafter) has demonstrated that there is a direct relationship between the signal obtained from a photoelectric aerosol sensor and the proportion of material in a sample, assuming that the material is covered with a photoemitting substance.

To convert it into a photoemitting state it can be practical to first treat the material in the sample mechanically, to grind it for example. It may also be useful to dilute the sample before or during the heat treatment that generates the photoemitting state by adding an appropriate form of non-emitting inert solid.

In one alternative of the method an additional support in the form of an inert solid can be added to the sample before or during the heat treatment. The additional support is intended to adsorb the substance that generates the signal and is optionally present in the form of a vapor and to make it accessible to measurement.

It can also be practical to add a carrier, an inert gas for example, to the sample.

If the sample has been properly prepared, the material can be continuously submitted to photoemission measurement and a corresponding continuous result signal obtained.

If the sample contains more than one photoemitting material, some or all of the sample can be converted into different photoemitting states and submitted to photoemission measurement, with empirical data obtained from corresponding reference samples or corresponding data obtained from calibration being taken into consideration during quantitative detection of the materials.

If the material is an organic material and the photoemitting substance that covers the submicrometric particles is a poly-aromatic hydrocarbon, it will be practical to heat the sample to 600 to 1000° C. and preferably to 750 to 850° C. to convert it to a photoemitting state.

The quantitative detection method of the present invention for detecting the proportion of a material in a sample, can be used in various ways. For example, if the measurement is continuous, the empirical signal can be used as a control signal for controlling or regulating a combustion process.

In another approach to applying the method in accordance with the present invention, the result of the detection of the material can be employed to verify the quality of the sample (a foodstuffs sample for example).

An appropriate device for quantitative detection features a photo-detecting sensor that emits an electric empirical signal, a unit upstream of the sensor that generates photo-emitting material, an electronic unit downstream of the sensor that determines the proportion of material in the sample from the signal obtained from that measurement in conjunction with empirical data obtained from a reference sample containing a previously detected quantity of the material or by using data obtained for the material by calibration, displays the resulting value or emits it in the form of a digital or electronic value. The unit upstream of the sensor can be a unit for heat-treating the sample if the material can thereby be converted into a photoemitting state. When the material is organic, the heat-treating unit should be adjustable to a prescribed temperature of 600 to 1000° C.

A unit for introducing a non-emitting inert solid and/or a unit for introducing more support can be optionally positioned upstream of the heat-treating unit in the methods hereintofore described.

When the device is employed for continuous detection of the material, an accessory for continuously supplying the sample can be provided and the electronic unit can be designed to continuously output the empirical signal. A control-or-regulating unit can for practical purposes be provided downstream of the electronic unit.

The teaching in accordance with the present invention provides a rapid and reliable device for samples of combustible material or material with a combustible portion.

The results of sample detection or analysis can be employed with coal for example for product monitoring and for equipment operations and/or process control in harvesting and processing, trade, and power-plant exploitation. Individual coal-dust burners can be directly controlled in accordance with how much coal or coal equivalent is supplied. The combustion process can also be regulated by incorporating exhaust analysis.

The sequence will now be described.

A fluid sample, of coal dust for example, is produced and heated.

Heat treatment produces an exhaust-gas aerosol covered with poly-aromatic hydrocarbons (PAH) depending on the organic content of sample on the heat (temperature, duration, etc.), and on the composition of the ambient gas.

The poly-aromatic hydrocarbon coverage of the flowing exhaust-gas aerosol is measured by on-line aerosol photoemission.

The method and device in accordance with the present invention will now be specified with reference to the accompanying drawing, and empirical results of the detection of material in a sample will be provided. The steps employed in this research are essentially the same as those of the empirical method. No unit for evaluating and comparison and for generating a signal for controlling the process was employed for this research. The procedure of extracting a sample from a process was simulated.

Steps involved in the method

A.

Extraction of a sample during processing or dispersing a sample through a carrier (air, nitrogen, oxygen, etc.)

continuously or discontinuously continuous or discontinuous forwarding of the sample.

B.

Conditioning of a dusty sample by heat treatment (e.g. exposure to heat, flash drying, or laser)

B.1

Use of one or more temperatures.

B.2

Conditioning (e.g. dilution, addition of an inert supplementary aerosol, or drying) of the submicrometric aerosol sample.

C.

Analysis unit (commercial sensor unit)—electrostatic filter for absorbing already charged particles, ultraviolet-radiation unit, and electrometer and amplifier.

D.

Interpretation unit.

BRIEF DESCRIPTION OF THE DRAWINGS

Figure 1:
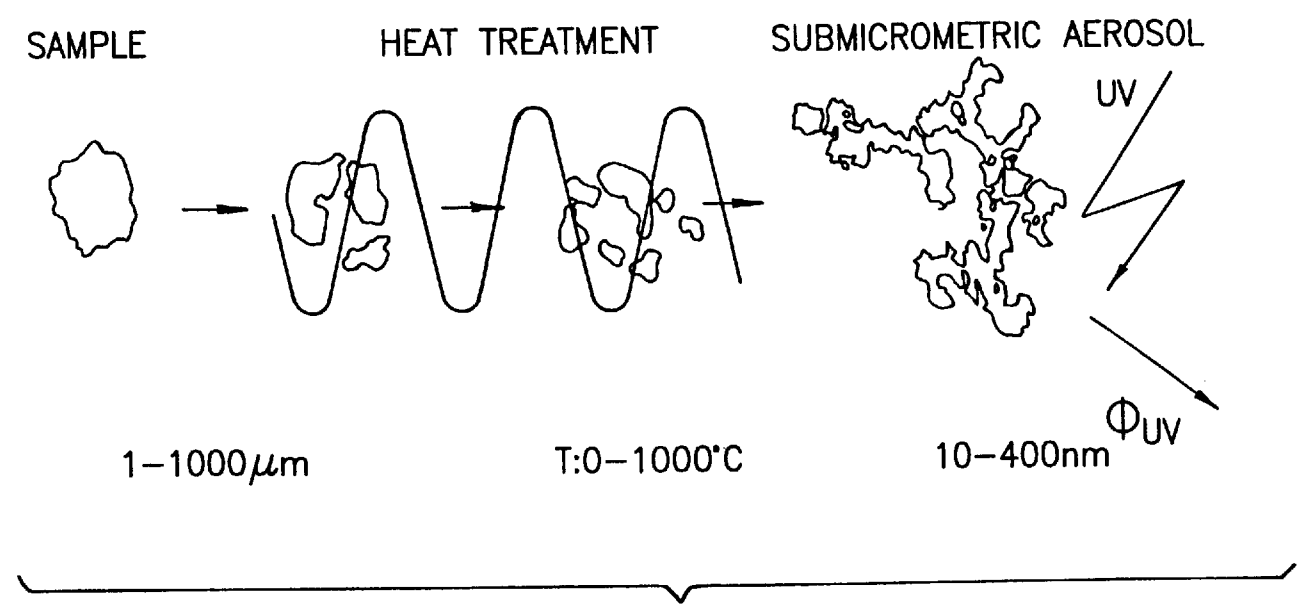

FIG. 1 illustrates the method of converting a sample by heat treatment and measurement of the submicrometric aerosol.

FIG. 2 is a schematic illustration of the device for measurement and signal generation.

FIG. 3A is an illustration of the principle of aerosol photoemission (APE) and FIG. 3B is an illustration of an ultraviolet-irradiation unit.

FIG. 4 is a graph of signal curves obtained by quantitative measurement.

FIG. 5 is a graph of signal curves obtained by qualitative measurement (where PAS stands for "photoelectric aerosol sensor").

Figure 6:
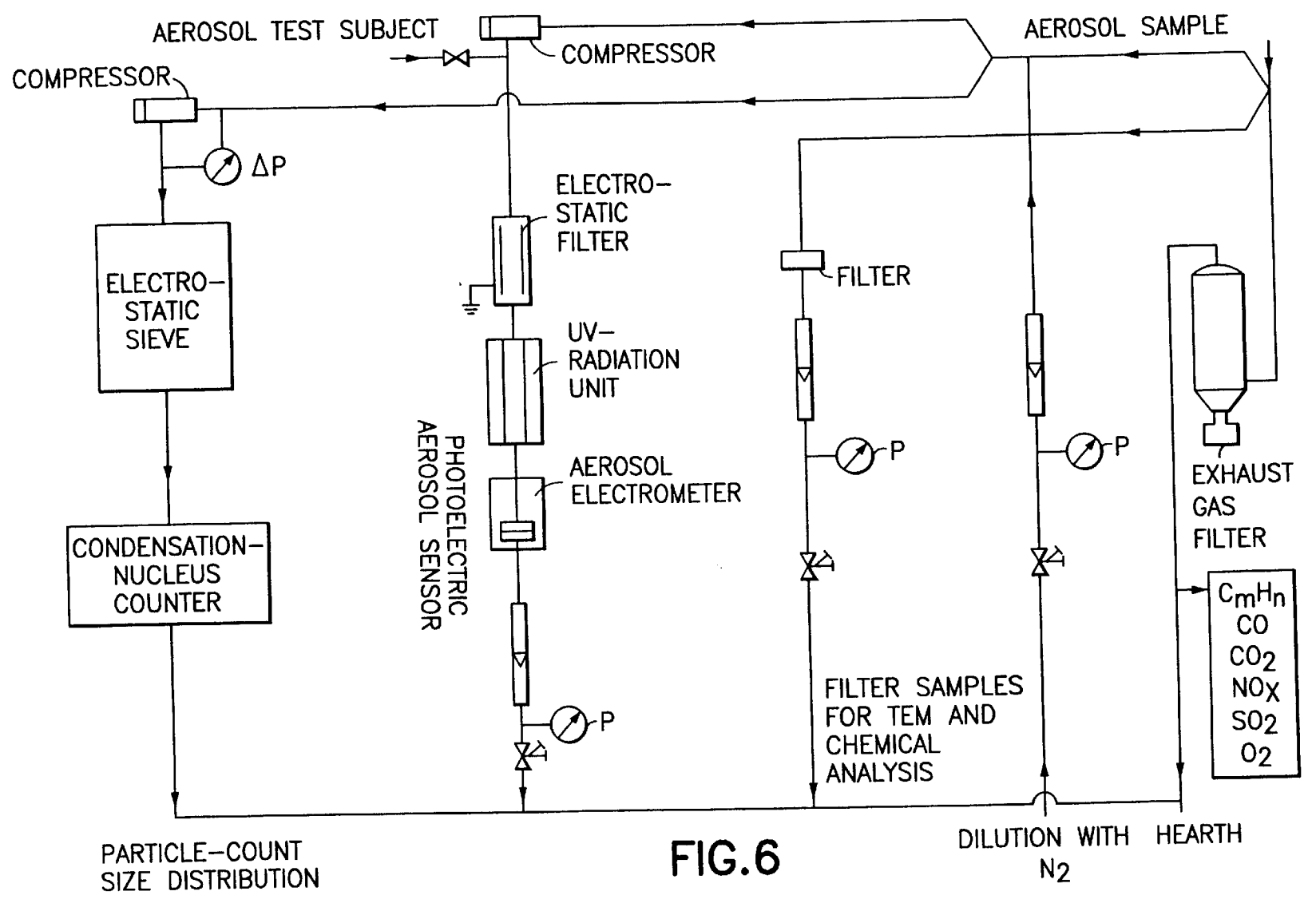

FIG. 6 illustrate a device for research to detect material in a sample.

DETAILED DESCRIPTION OF THE INVENTION

FIG. 1 is a schematic illustration representing the conversion of a particle of dust by heat treatment followed by measurement of the submicrometric combustion aerosol. The diameter $D_I$ of one particle in the sample is originally on the order of 1 to 1000 $\mu$m. Heat treatment is accompanied by exposure to temperatures of up to approximately 1000° C. The result is a submicrometric combustion aerosol with particle diameters $D_{II}$ of approximately 10 to 400 nm. Radiation with ultraviolet light generates an ionizing current $\Phi_{uv}$ that depends on the parameters T, $D_I$, and $D_{II}$ etc.

FIG. 2 illustrates the sequence of modules in a device for detecting material in a sample. The sample is prepared by direct extraction from a process and by diluting it with a carrier (e.g. air). It is then heated in a capillary radiation furnace 1 or by some other procedure.

An electrostatic filter can be interposed upstream of the analysis section (2). This can if necessary be followed by irradiation (UV) with ultraviolet light, measurement of the charge, and amplification of the empirical signal. The signal can be processed for example and compared with stored data and a process-control signal generated in an attached processor, a personal computer for example.

FIG. 3(A) illustrates a model of a submicrometric agglomerated particle with adsorbates excited by ultraviolet radiation to the extent of emitting a photoelectron (by the principle of aerosol photoemission, APE, where hν≡light-quantum energy and $\Phi_0$=exit work). FIG. 3(B) illustrates an ultraviolet-radiation unit that allows continuous photoemission measurements to be carried out on a flowing aerosol sample.

FIG. 4 illustrates the relationship between a photoelectric aerosol-sensor signal, temperature, and coal-dust input. The signal decreases with input.

It also decreases as the proportion of inert material in the sample increases.

Each of the parameters employed here (especially T, λ, residence time, etc.) attains its maximum for various types of coal at a temperature of approximately 800° C.

The samples employed for these qualitative measurements were samples of 300, 225, 150, and 75 mg/h of coal in 0.6 $m^3$ of air as a carrier.

In the foodstuffs field, samples of various masses (approximately 300, 225, 150, and 75 mg/h) of flour in 0.6 $m^3$ of the same carrier were tested with the same processing parameters.

The results were similar to those obtained for coal. There is in particular a comparable relationship between mass and temperature.

FIG. 5 illustrates the results of qualitative measurements on various samples.

The subject used was foundry sand that had been recycled various numbers of times (0 and 4 or 5) in a processing plant.

A maximum signal was detected at 900° C. for sand that had been reprocessed 0 or 4 times and almost no signal for sand that had been reprocessed 5 times.

FIG. 6 illustrates the apparatus employed to detect the content of material in a sample. The components of the accessories employed to measure the sample aerosol are an electrostatic filter, an ultraviolet-irradiation unit, and an aerosol electrometer.

This apparatus allows several tests to be conducted simultaneously:

1)

Measurement of the photoelectric charge generated on the flowing aerosol sample by the ultraviolet unit. This measurement is obtained with a photoelectric aerosol sensor (PAS).

2)

Testing the relationship between the PAS and the polyaromatic hydrocarbon (PAH) concentration of the exhaust aerosol by wet-chemistry gel chromatography of the PAH from samples filtered out of the exhaust.

3)

Testing the surface correlation by measuring particle-size distribution with an electrostatic sieve and a condensation-particle counter.

4)

Visibilization of the microstructures of the signal-generating particle by displaying them in a transmission electron microscope (TEM). The particles are collected by electrostatic precipitation onto standard carbon-coated TEM gratings.

Specifications of the (capillary) furnace employed in the research are discussed herein:

| | |
|---|---|
| Length: | 600 mm |
| Inside diameter: | 5.4 mm |
| Carrier flow rate | approximately 0.6 m³ |
| Residence time: | approximately 0.125 sec |
| Vacuum | 15 mbars |

The temperatures herein are peak values.

Coal dust and other substances (approximately 400 mg/h, particles>300 nm) were dispersed in air, heated, and analyzed.

Results

The tests were carried out at peak temperatures of 600 to 1000° C.

The exhaust was cooled and diluted with air (1:3) and $N_2$, corresponding to an absolute dilution of 1:15 prior to analysis.

Air flow, dilution, and ultraviolet intensity were selected to ensure as simple as possible relationships between PAS signal, PAH concentration, and probe material content at satisfactory sensitivity.

The following result, valid for various samples, concerns the distribution of particle size.

Both the (aerodynamic) diameter and the count concentration of the particles are maximal at approximately 800° C., the temperature of the maximal PAS signal, for many samples.

The particle-size distribution and count concentration shift only slightly when the temperature is increased to 1000° C. The associated PAS signal decreases, however, more than 75%. This result agrees well with the wet-chemistry PAH concentrations. At low temperatures (<800° C.) fewer and smaller agglomerates are generated, and the PAS signal increases again.

TEM images demonstrate that the agglomerates at all temperatures are essentially primary spherules with diameters less than 50 nm. They probably form during the cooling phase.

We claim:

1. Method of quantitatively detecting material in a sample, wherein the material is in the form of submicrometric particles covered by a photoemitting substance, comprising exciting the material in the sample to a photoemitting state comprising heating the sample;

subjecting the material, while in the photoemitting state, to photoemission measurement, and determining the proportion of the material in the sample from the signal obtained from the photoemission measurement in conjunction with empirical data obtained from a reference sample containing a previously detected quantity of the material or by using data obtained for the material by calibration.

2. Method as in claim 1, further comprising diluting the sample before or during the exciting of the material to the photoemitting state, by adding a non-emitting inert solid.

3. Method as in claim 1 or 2, further comprising adding an additional support in the form of an inert solid, to the sample, before or during the heating step.

4. Method as in claim 1, further comprising adding a carrier to the sample.

5. Method as in claim 4, wherein the carrier is an inert gas.

6. Method as in claim 1, wherein the material is continuously subjected to photoemission measurement and a corresponding continuous result signal obtained.

7. Method as in claim 6, wherein the material is an organic and combustible material and the continuous result signal is employed as a parameter for controlling or regulating a combustion process.

8. Method as in claim 1, wherein the material is an organic material and the photoemitting substance that covers the submicrometric particles is a poly-aromatic hydrocarbon.

9. Method as in claim 8, wherein the sample is heated to 600 to 1000° C.

10. Method as in claim 9, wherein the sample is heated to 750 to 850° C.

11. Method as in claim 1, wherein the material is a foodstuff and the determined proportion of the material is employed to verify the quality of the sample.

12. Method as in claim 1 further comprising irradiating the heated sample with UV irradiation to excite photoelectron emission.

13. Device for the quantitative detection of material in a sample, wherein the material is in the form of submicrometric particles covered by a photo-emitting substance, comprising a photo-detecting sensor that produces an electric empirical signal in response to photoemissions, a heat-treating unit upstream of the sensor, said unit including a heater for heating the material in the sample to a photoemitting state to produce photoemissions, an electronic unit downstream of the sensor that determines the proportion of the material in the sample from the electrical empirical signal in conjunction with empirical data obtained from a reference sample containing a previously detected quantity of the material or by using data obtained for the material by calibration, and displays the resulting proportion or emits resulting proportion in the form of a digital or electric value.

14. Device as in claim 13, wherein the heat-treating unit is adjustable to a prescribed temperature of 600 to 1000° C.

15. Device as in claim 14, further comprising a unit for introducing a non-emitting inert solid diluent upstream of the heat-treating unit.

16. Device as in claim 15, further comprising a unit for introducing a non-emitting inert solid support upstream of the heat-treating unit.

17. Device as in claim 13, further comprising an accessory for continuously supplying the sample, whereby the electronic unit is designed to continuously emit the digit or electric value.

18. Device as in claim 17, further comprising a control- or-regulating unit downstream of the electronic unit to convert the digital or electric value to a control signal.

\* \* \* \* \*